US010426877B2

(12) United States Patent
Sablotsky et al.

(10) Patent No.: US 10,426,877 B2
(45) Date of Patent: Oct. 1, 2019

(54) BREAST MILK EXPRESSION APPARATUS AND SYSTEM

(71) Applicant: IMALAC, LLC, Miami, FL (US)

(72) Inventors: Noreen Gordon Sablotsky, Miami, FL (US); Rachael Sablotsky Kish, Miami, FL (US); Kathryn Garriott Sablotsky, Charleston, SC (US); Scott R. Arp, Miami, FL (US); William Thomas Bales, Miami, FL (US); Paul John Grata, Miami Lakes, FL (US); Victor M. Gamez, Fort Lauderdale, FL (US); Damian H. Tomlin, Coral Springs, FL (US)

(73) Assignee: IMALAC, INC., Miami, FL (US)

( * ) Notice: Subject to any disclaimer, the term of this patent is extended or adjusted under 35 U.S.C. 154(b) by 215 days.

(21) Appl. No.: 15/431,644

(22) Filed: Feb. 13, 2017

(65) Prior Publication Data
US 2018/0228949 A1 Aug. 16, 2018

(51) Int. Cl.
*A61M 1/06* (2006.01)
(52) U.S. Cl.
CPC ............ *A61M 1/066* (2014.02); *A61M 1/06* (2013.01); *A61M 2205/3368* (2013.01); *A61M 2205/3389* (2013.01); *A61M 2205/36* (2013.01); *A61M 2205/50* (2013.01); *A61M 2205/8206* (2013.01)
(58) Field of Classification Search
CPC ........ A61M 1/06; A61M 1/062; A61M 1/064; A61M 1/066; A61M 1/068; A61M 2210/1007
See application file for complete search history.

(56) References Cited

U.S. PATENT DOCUMENTS

| 6,461,324 B1 * | 10/2002 | Schlensog | A61M 1/06 604/74 |
| 2003/0073951 A1 * | 4/2003 | Morton | A61B 5/6834 604/73 |
| 2006/0106334 A1 | 5/2006 | Jordan | |

(Continued)

FOREIGN PATENT DOCUMENTS

WO WO2016/014494 A1 1/2016

OTHER PUBLICATIONS

Toworld 18 New Electronic Breast Massager Device Augmentation Lift, product description, downloaded Dec. 27, 2016, available at https://www.amazon.com/Toworld18-Electronic-Breast-Massager-Augmentation/dp/B00IZ4W2HM.

(Continued)

*Primary Examiner* — Kevin C Sirmons
*Assistant Examiner* — Leah J Swanson
(74) *Attorney, Agent, or Firm* — Gordon & Jacobson, P.C.

(57) ABSTRACT

A breast milk expression apparatus for manipulating a breast of a user includes an outer shell, and a plurality of circumferentially spaced inner pads coupled to the outer shell. The pads are configured to engage the breast of the user and configured for radial displacement. The breast milk expression apparatus further includes a compression unit coupled to the plurality of pads. The compression unit is configured to cyclically displace the pads radially inwardly against the breast to cause compression of the breast and, following compression of the breast, to permit displacement of the pads radially outwardly from the breast as the breast decompresses.

19 Claims, 9 Drawing Sheets

(56) References Cited

U.S. PATENT DOCUMENTS

2014/0378946 A1    12/2014   Thompson et al.
2015/0065994 A1     3/2015   Fridman et al.
2017/0112983 A1     4/2017   Thorne et al.

OTHER PUBLICATIONS

Hands-Free Compression for Breast Compression by Lilu., Aug. 22, 2016, as reprinted from Wayback Machine, archived at https://web.archive.org/web/20160822070905/wearlilu.com.

* cited by examiner

BREAST MILK EXPRESSION APPARATUS AND SYSTEM

BACKGROUND

1. Field

This disclosure relates to a breast milk expression apparatus and system.

2. State of the Art

Women's breasts are made of specialized tissues that produce milk. This includes glandular as well as fatty tissues. The milk-producing part of the breast is organized into 15 to 20 sections, called lobes. Within each lobe are smaller structures, called lobules, where milk is produced. The milk travels through a network of tiny tubes called ducts. The ducts connect and come together into larger ducts, which eventually exit the skin in the nipple. There is a considerable body of evidence in the literature on the proven and potential benefits of breast milk expression during lactation. These benefits include, but are not limited to: clearing clogged milk ducts, assisting milk to flow more freely through the ducts resulting in a decrease in time required and increase in quantity of milk expressed during any given single pumping event, creation of subjective physical pleasure and decrease in generalized breast pain, increase in the positive caloric nutritional value of the breast milk resulting from more complete emptying of all lactation tissue. Hand expression is often used as a viable method for milk extraction, and is more commonly recommended by leading lactation experts as a simultaneous adjunct to breast pumping.

SUMMARY

As will be appreciated from the following description, in accordance with at least one aspect, a breast milk expression apparatus and system can replace manual (by hand) milk extraction.

According to one aspect, further details of which are provided below, a breast milk expression apparatus includes an outer shell, and a plurality of circumferentially spaced inner pads coupled to the outer shell. The pads are configured to engage a breast of the user and configured for radial displacement. The breast milk expression apparatus further includes a compression unit coupled to the plurality of pads. The compression unit is configured to cyclically displace the pads radially inwardly against the breast to cause compression of the breast and, following compression of the breast, to permit displacement of the pads radially outwardly from the breast to allow for decompression of the breast.

The outer shell, which may be manufactured in multiple sizes, may have an inner surface that is generally concave. The inner surface may be convex near an axillary part of the breast. The sizes of the outer shell may correspond to bra cup sizes. The inner surface may be configured to engage a maximum possible volume of a user's breast tissue. The outer shell may define a central opening about which the plurality of inner pads are circumferentially spaced. The central opening may be dimensioned to receive a breastshield therethrough for engagement with the user's breast. Milk expressed during use of the breast milk expression apparatus may be directed by the breastshield away from the breast, such as to a collection bottle.

The pads that are coupled to the outer shell may be variously shaped and configured to engage the outer surface of a user's breast for breast manipulation to facilitate milk expression. Also, at least one of the pads may be heated.

The breast milk expression apparatus may include an outer cover that may cover the outer shell. The outer cover may function to protect the outer shell and/or the compression unit and may also provide a desired aesthetic look. The breast milk expression apparatus may also include an inner liner to cover the pads coupled to the outer shell. The inner liner may provide a comfort barrier between the skin of a user's breast and the pads. In one embodiment, the outer cover and the inner liner are coupled together to form an encasement for the breast milk expression apparatus. The outer cover, inner liner, and the encasement may be removable from the breast milk expression apparatus.

In one embodiment of the breast milk expression apparatus, the compression unit includes a cable banded about and through the plurality of pads, and a drive unit coupled to the cable and the outer shell. The drive unit is configured to tighten the cable about the pads to cause the pads to compress the breast and is configured to subsequently loosen the cable about the pads, permitting the breast to expand and decompress.

Each pad may define a circumferential channel through which the cable extends. The circumferential channel may permit relative movement between the cable and the pad. The drive unit may include an electric motor configured to drive a transmission system to alternate tension in the cable. In one embodiment, the drive unit is configured to receive at least one of power and control setting signals from a controller. The drive unit may vary one or more of a pressure applied by the pads to the breast, a duration of compression and decompression, and a heating level of the pads.

At least one of the pads and the outer shell may be made of one or more polymeric materials, such as ABS, nylon, polyurethane, and silicone, and may have a Shore hardness of 10 A to 90 D.

According to another aspect, further details of which are provided below, a breast milk expression system includes at least one breast milk expression apparatus configured to cyclically compress and allow decompression of a breast of a user, at least one strap coupled to the breast milk expression apparatus and configured to position the breast milk expression apparatus on a user's breast, and a controller configured to control the operation of breast milk expression apparatus. The breast milk expression apparatus of the breast milk expression system may be any of the previously described breast milk expression apparatuses. The breast milk expression system may be used for milk expression of one or both breasts of a user, individually or simultaneously.

The controller may be configured to control one or more of breast manipulation pressure, temperature, and manipulation speed. The controller may be wired or wireless. The breast milk expression apparatus of the system may include a power supply to power at least one of the breast milk expression apparatuses and the controller. The controller may include a power supply to power at least one of the controller and one or both of the breast milk expression apparatuses. The controller and/or the breast milk expression apparatus(es) may be operated through a computing device, such as a smart phone, tablet computer, smart watch, or other computing device communicatively coupled to the controller and/or the breast milk expression apparatus(es).

In one embodiment of the system, two breast milk expression apparatuses and a set of straps are arranged so that they may be worn like a bra, such as any type of bra known in the art. The straps may be integrated or otherwise attached to the aforementioned cover and/or liner. The straps are adjustable for personalized fit to the wearer. The straps may permit separation of the two breast milk expression apparatuses from one another so that, for example, the straps can be rearranged to wear one breast milk expression apparatus independently of the other breast milk expression apparatus. The breast milk expression apparatuses may be removable from the straps.

In one embodiment, a breast milk expression system includes a separate bra for supporting breasts of a user and at least one breast milk expression apparatus coupled to the bra and positioned between the bra and the breast of the user. The breast milk expression apparatus may be removably coupled to the bra so that the breast milk expression apparatus can be decoupled from the bra so that that bra can be used without the breast milk expression apparatus. The bra may be any type of bra known in the art. The bra may be integrated with or otherwise attached to the aforementioned cover and/or liner.

DETAILED DESCRIPTION OF THE PREFERRED EMBODIMENTS

Figure 1A:
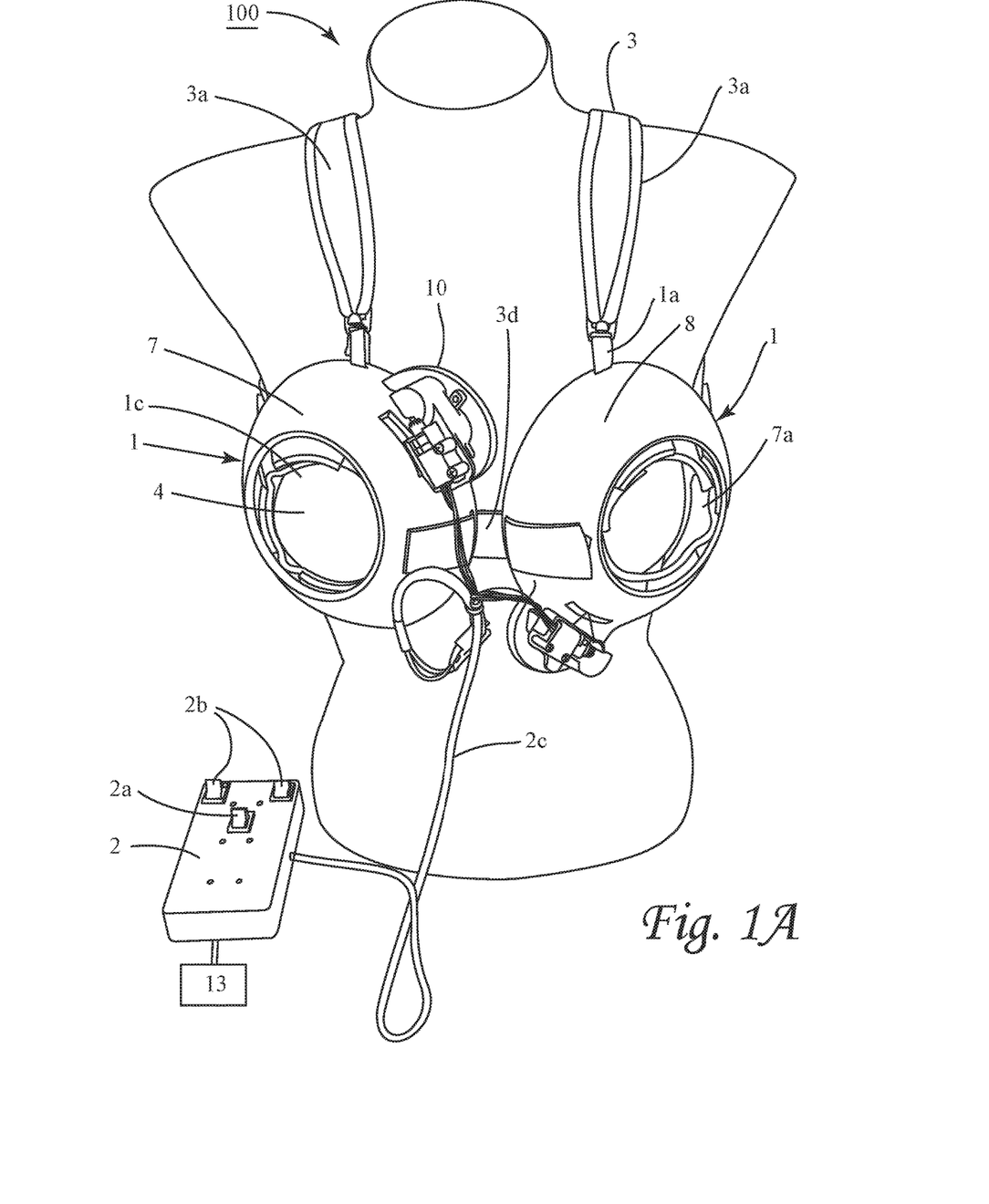
FIGS. 1A and 1B show an embodiment of a breast milk expression system arranged on a torso.

FIG. 1A shows one embodiment of a breast milk expression system 100 that includes two breast milk expression apparatuses 1 (hereinafter referred to as "expression apparatuses"), a controller 2 coupled to the expression apparatuses 1 via a power and control cords 2c, and a plurality of straps 3 for arranging the expression apparatuses 1 on the breasts 4 of a user and for connecting the expression apparatuses 1 together. Preferably, the straps 3 and expression apparatuses 1 are arranged and used like a bra to facilitate hands-free operation of one or both of the expression apparatuses 1. For example, the straps 3 may support the expression apparatuses 1 over the breasts 4 without a user holding the expression apparatuses 1 in place, either when the expression apparatuses are on or off. Two expression apparatuses 1 are shown included with the system 100 in FIG. 1A, where one expression apparatus 1 corresponds to each breast. While two expression apparatuses 1 are shown, they may operate independently or together (e.g., simultaneously). Also, in other embodiments of the system, only one expression apparatus 1 may be included and a user may alternate its use from one breast to another as desired. Each expression apparatus 1 is configured to manipulate the tissue of the corresponding breast 4 based on a control input from the controller 2, as described in greater detail below. The milk expression system 100 can be used before, during, and/or after breast pumping or nursing to facilitate lactation and improve milk production and flow.

Figure 1B:
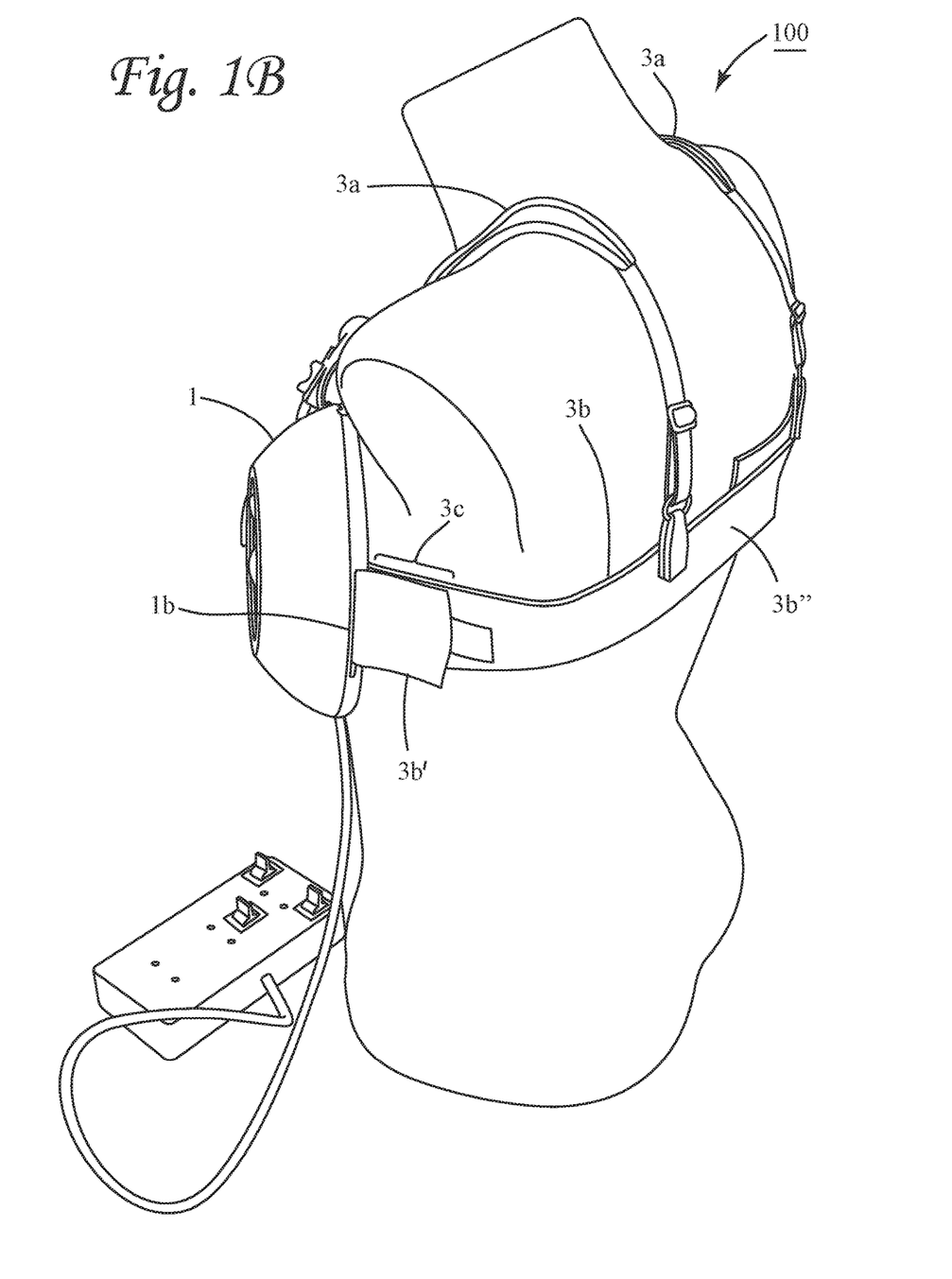

The plurality of straps 3 includes adjustable top straps 3a, each of which is attached at a top location 1a of the expression apparatuses 1. Each top strap 3a is configured to extend upward from a corresponding expression apparatus 1 and go over the shoulders and down the back of the user to connect to a corresponding adjustable side or back strap 3b (hereinafter referred to as a "side strap"), as shown in further detail in FIG. 1B. The top straps 3a may be padded for user comfort. Each side strap 3b has a first end 3b' coupled to an outer, side location 1b (FIG. 1B) of a corresponding expression apparatus 1, and has a second end 3b" opposite the first end 3b'. The side strap 3b extends from the expression apparatus 1 around the side of the user's torso towards the center of the user's back, where the second ends 3b" of each side strap 3b may be fastened together. The second ends 3b" of the side straps 3b may include hooks and loops (not shown) for fastening the second ends 3b" together. Also, the length of the side straps 3b may be adjustable at either end 3b', 3b" thereof. For example, in the embodiment shown in FIG. 1B, each expression apparatus 1 may have a loop or slot on its side 1b through which a first end 3b' of the side strap 3b can be wrapped. The first end 3b' may have hooks or loops and an overlapping portion 3c of the strap 3b may have mating hooks or loops to adjust the length of the side strap 3b.

In the shown embodiment, a center strap 3d (FIG. 1A) between the user's breasts 4, couples the expression apparatuses 1 together. The expression apparatuses 1 may have loops or slots on inner side locations 1d of the expression apparatuses 1 for coupling ends of the center strap 3d thereto, similar to the loops or slots on the outer side locations 1b of the expression apparatuses 1 for coupling side straps 3b. The length of the center strap 3d may also be adjustable to adjust the spacing between the expression apparatuses 1. The center strap 3d may permit decoupling or separation of the two expression apparatuses 1 from one another and from the center strap 3d. For example, the ends of the strap 3d may be detachably connected to the side locations 1d of respective expression apparatuses 1. Also, the center strap 3d may be formed as two parts that are connectable at respective ends between the side locations 1d, in the same manner that side straps 3b connect at ends 3b" between side locations 1b of expression apparatuses 1.

Figure 1C:
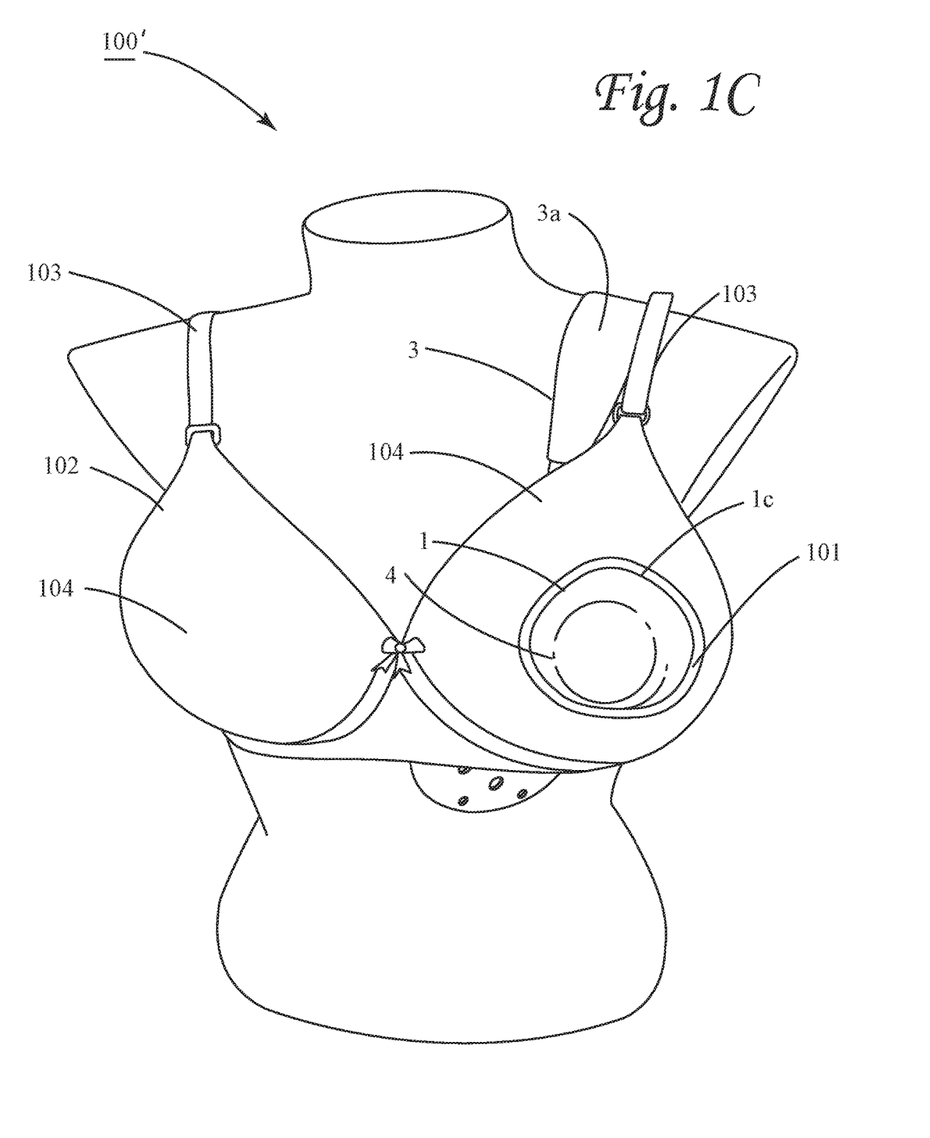
FIG. 1C shows an embodiment of a breast milk expression system that includes a bra and a breast milk expression apparatus of the system of FIGS. 1A and 1B.
Figure 2:
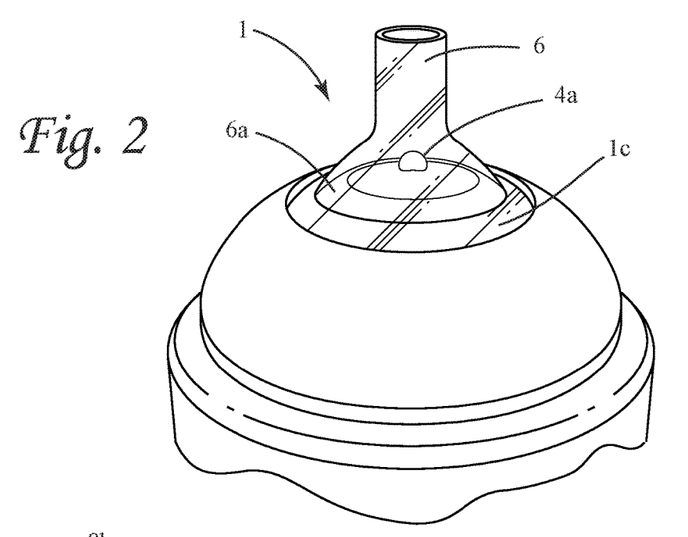
FIG. 2 shows a top perspective view of a breast milk expression apparatus of the system of FIGS. 1A and 1B along with a breastshield.

While the system 100 shows straps 3 and expression apparatuses 1 worn like a bra, in one embodiment shown in FIG. 1C, a system 100' includes a separate bra 102 and at least one breast expression apparatus 1 (partially covered by the bra 102 in FIG. 1C) coupled to the bra 102 and positioned between the bra 102 and the breast 4. The bra 102 may have breast cups 104 attached to one or more straps 103, and one breast expression apparatus 1 may be removably coupled to an inside of a corresponding breast cup 104 so that the expression apparatus 1 can be positioned between the user's breast 4 and the cup 104 of the bra 102. The expression apparatus 1 may be coupled to the breast cup 104 using one or more fasteners or simply held in position by a friction or interference fit between the breast cup 104 and the expression apparatus 1. In such an embodiment, the expression apparatus 1 can be decoupled from the 102 bra (e.g., the cup 104 of the bra 102) so that that bra 102 can be used without the expression apparatus 1.

One or both of the cups 104 of the bra 102 may be solid (e.g., left cup in FIG. 1C) or may have at least one opening 101 (e.g. right cup in FIG. 1C). In the example shown in FIG. 1C, the opening 101 is aligned with opening 1c of the expression apparatus 1. The opening 101 may be sized to be at least as large as the opening 1c.

Although FIG. 1C shows one example bra, the aforementioned bras may be any type of bra known in the art, including, without limitation, a halter bra, a bandeau bra, a balconette bra, a contour or molded cup bra, a convertible bra, a demi cup bra, a full cup bra, a mastectomy bra, a maternity and nursing bra, a minimizer bra, a padded bra, a plunge bra, a push-up bra, a racerback bra, a shelf bra, a sports bra, a strapless bra, a T-shirt bra, and a U-plunge bra.

In use, the expression apparatuses 1 of the breast milk expression system 100 are positioned over and about the breasts 4. As shown in FIGS. 1A to 3, the expression apparatuses 1 define a central opening 1c in which a nipple 4a of the breast 4 can be positioned. The central opening 1c provides access for a user to position a breastshield 6 (FIG. 2) within the opening 1c over the nipple 4a to facilitate milk collection (e.g., into a bottle or by breast pumping) while using the system 100. Preferably, the diameter of the central opening 1c is large enough to accommodate a range of sizes of breastshields 6 being marketed. For example, the diameter of the central opening 1c may be large enough to accommodate a breastshield having a diameter of 36 mm.

Figure 3:
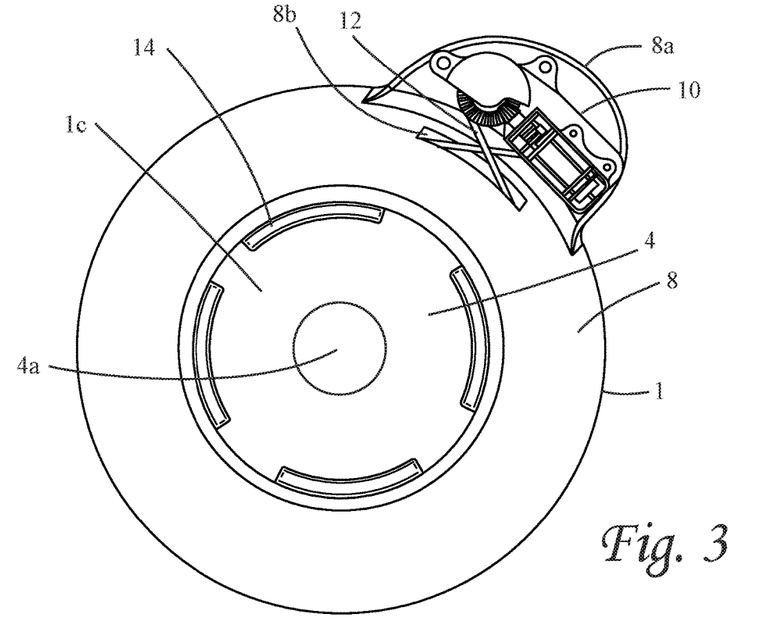
FIG. 3 illustrates a top view of one of the breast milk expression apparatuses shown in FIG. 1A.

In the breast milk expression system 100, each expression apparatus 1 is functionally identical. FIG. 3 shows a view of one of the expression apparatuses 1 shown in FIG. 1A. The expression apparatus 1 has an outer shell 8, which may be made of ABS, nylon, polyurethane, or silicone having a Shore hardness of about 10 A to 90 D. The outer shell 8 has an inner form that is generally concave to conform to the contour of a plurality of pads 14, further details of which are provided below. Also, in one embodiment of an expression apparatus 201 (FIG. 7), an outer shell 208 has a portion 208c (FIGS. 9, 10) that is configured to extend over or near an axillary part 4b (FIG. 10) of the breast 4, as shown in FIG. 10. An inner surface 208d (FIG. 9) of the outer shell 208 is generally concave, and may be convex on portion 208c to conform to the contour of the axillary part 4b (FIG. 10) of the breast 4.

The expression apparatus 1 may include an outer cover 7 that may cover the outer shell 8 and/or the compression unit. The outer cover 7 may function to protect the outer shell and/or the compression unit and may also provide a desired visual appearance. The expression apparatus 1 may also include an inner liner 7a to cover the pads 14 coupled to the outer shell 8. The inner liner 7a may provide a comfort barrier between the breast 4 and the pads 14. The outer cover 7 and/or inner liner 7a may be removable from the expression apparatus 1. The outer cover 7 and/or the inner liner 7a may be made from one or more of polyester, cotton, spandex, silk, or other preferably comfortable-to-the-touch material. In one embodiment, the outer cover 7 and the inner liner 7a are coupled together to form an encasement for the expression apparatus 1. While the outer shell 8 is shown as being a generally solid structure, in at least one embodiment, the outer shell 8 may be have openings and may take the form of a frame or cage-like structure, which may make the shell 8 lighter and more comfortable for the user to wear.

In at least one embodiment, the breastshield 6 may be incorporated into the expression apparatus 1. For example, a flange 6a (FIG. 2) of the breastshield 6 may be removably attachable to and detachable from the outer shell 8, outer cover 7, or inner liner 7a. For example, the flange 6a of the breastshield 6 may removably engage (e.g., adhesively, friction fit, interference fit, etc.) the outer shell 8, outer cover 7, or inner liner 7a to retain the breastshield 6 connected thereto when in use and permits the breastshield 6 to be detached from the outer shell 8, outer cover 7, or inner liner 7a, without damage to any of the breastshield 6, the outer shell 8, outer cover 7, and inner liner 7a.

The outer shell 8 and pads 14 may be made from one or more fabric materials. The fabric used for the outer shell 8 may be stiffer than the fabric used for the pads 14. Portions of the fabric(s) used may be reinforced or stiffened, such as with a wire, similar to an underwire of a bra. Such a reinforcement or stiffener may be made of at least one of metal, plastic, or resin, for example. Further, the outer shell 8 may be formed as a fabric covered cage or mesh, which may improve comfort for the user, as mentioned above.

The outer shell 8 has a deck 8a extending generally horizontally from a side of the outer shell 8. In a case where the outer shell 8 is made of fabric, as discussed above, the deck 8a may be formed from stiff fabric and may be reinforced with a reinforcement member or stiffener (e.g., wire), as noted above. The deck 8a is configured for mounting and supporting a drive unit 10, further details of which are provided below. For example, the drive unit 10 may be adhesively or mechanically attached to the deck 8a. The outer shell 8 also defines a circumferential through-slot 8b proximate the deck 8a which is configured to route a cable 12, which is driven by the drive unit 10. As will be described in greater detail hereinafter, the drive unit 10 and the cable 12 operate to cyclically compress and allow decompression of the pads 14 against the breast 4 to manipulate the tissue of the breast 4. The drive unit 10 and the cable 12 may thus be considered an embodiment of what is hereinafter termed a "compression unit." Other embodiments of a compression unit are possible. For example, in one embodiment a geared belt or notched strap may be used in place of the cable 12 and such a geared belt or notched strap may be moved by a releasable ratcheting arrangement to tighten the belt or strap and allow the belt or strap to be loosened.

Figure 4:
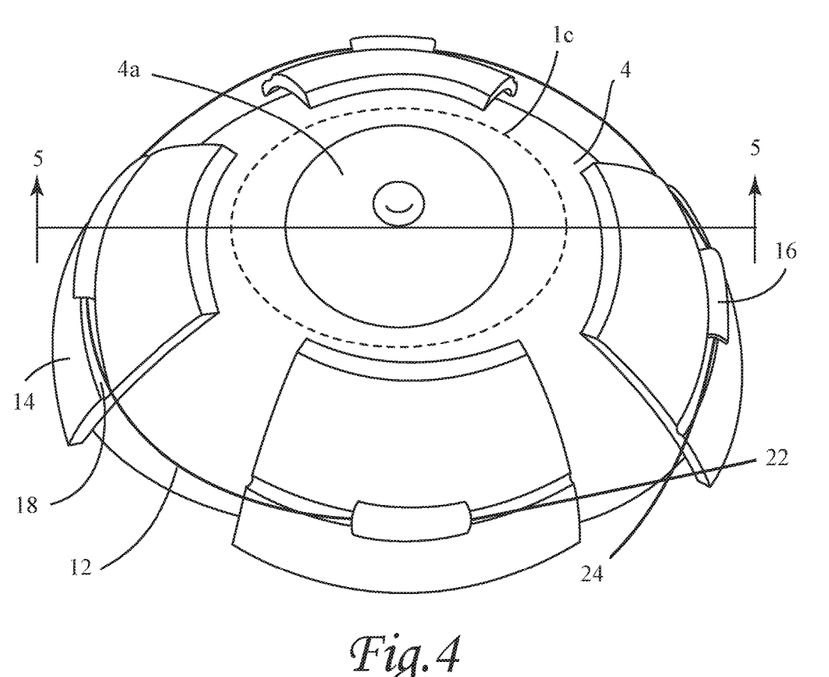
FIG. 4 illustrates the breast milk expression apparatus shown in FIG. 3 with an outer shell omitted to show an arrangement of pads of the breast milk expression apparatus located relative to a breast of the user.

As shown in FIG. 3, the outer shell 8 partially covers a plurality of the pads 14. FIG. 4 shows the pads 14 with the outer shell 8 omitted for clarity. The pads 14 are spaced circumferentially from one another around the central opening 1c. The pads 14 may be made of flexible material, such as polyurethane or silicone. The pads 14 may have a Shore hardness of 10 A to 90 D. The pads 14 are configured to be radially displaced inwardly for a certain period of time by action of the drive unit 10, which moves the pads 14 toward and against the breast 4, compressing the tissue of the breast 4. When the action of the drive unit 10 reverses, the compression ends and the pads 14 can radially expand due to radially outward pressure on the pads 14 applied by the breast 4. This compression/decompression cycle can repeat by operation of the drive unit 10. The parameters of that cycle may be adjusted, start, or stopped by the controller 2, which is communicatively coupled to the drive unit 10, either via a wired connection 2c or a wireless connection (e.g. infra-red, Wi-Fi, Bluetooth, etc.).

In one embodiment at least one or more of the pads 14 may have a heating element (not shown) to warm the breast 4 during operation of the expression apparatus 1. Also, optionally, on an inner side of the pads 14 (e.g., side facing the breast 4), the pads 14 may have one or more padding layers (not shown), such as to improve user comfort and fit. In one embodiment, the pads 14 may contain a gel-like material to facilitate heat dispersion. The gel-like material may include silicone.

Figure 5:
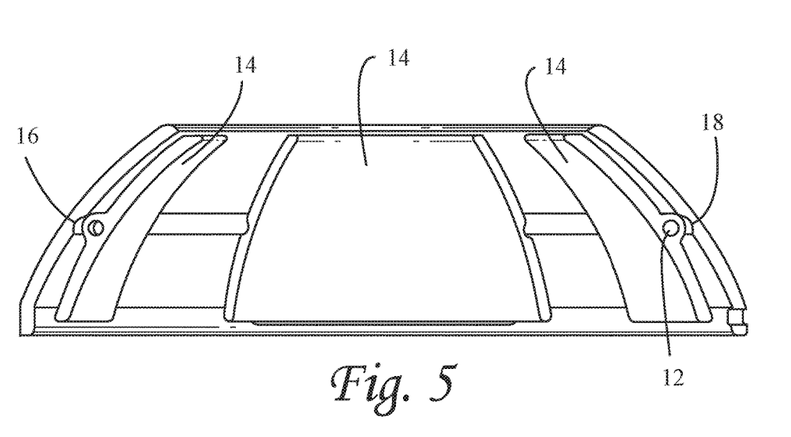
FIG. 5 is a view of the pads of FIG. 4 along section 5-5 shown in FIG. 4, and with the breast omitted.

As shown in FIGS. 4 and 5, each pad 14 defines an enclosed cable channel 16 and a groove 18 that extend circumferentially on an outer side of the pad 14. The cable channels 16 and grooves 18 are configured to route the cable 12 around the plurality of pads 14, thereby coupling the pads 14 together. The cable 12 crosses over itself (preferably without touching) between two of the pads 14, as shown in FIGS. 3 and 4. While only one cable channel and groove are shown for each pad 14, each pad 14 may have more than one cable channel and groove to accommodate more than one cable, as will be described in greater detail below.

Figure 6:
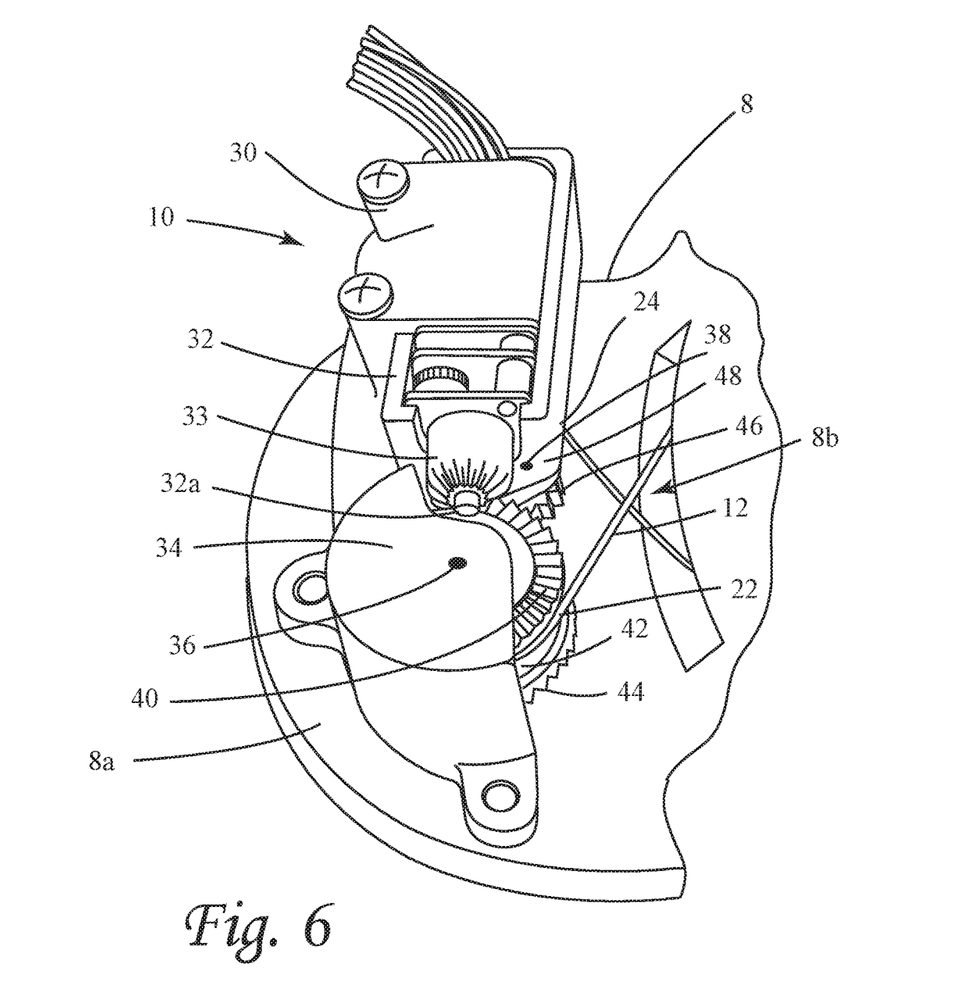
FIG. 6 is an enlarged view of a drive unit of one of the breast milk expression apparatuses shown in FIG. 1A.

As shown in FIG. 6, the cable 12 extends through the circumferential slot 8b in the outer shell 8 and crosses over itself with a first end 22 and a second end 24 extending to the drive unit 10. In the embodiment of the drive unit 10 shown in FIG. 6, the drive unit 10 includes an electric motor 30, a gearbox 32 driven by the motor 30, and a transmission system 34 driven by the motor 30 and connected to the first and second ends 22 and 24 of the cable 12. The motor 30 may be an AC or DC electric motor powered by a power supply included with the expression apparatus 1, such as a battery, or by an external power supply, such as a power supply (e.g., battery) located in the controller 2 and supplied via cord 2c (FIG. 1A). Also, the expression apparatus 1 or the controller 2 may have a power connector for receiving power from an electrical outlet, such as an AC outlet.

The motor 30 may be coupled to the gearbox 32 by one or more gears as is known in the art to drive a driving bevel gear 33 on an output shaft 32a of the gearbox 32. The transmission system 34 includes a first vertical shaft 36 and a second vertical shaft 38 that are driven by the driving bevel gear 33. The first shaft 36 rotates about a first vertical axis along a longitudinal length of the first shaft 36. A driven bevel gear 40 is secured to an upper end of the first shaft 36. The driven bevel gear 40 meshes with and is configured to be driven by the driving bevel gear 33 to rotate the first shaft 36 about the first axis. The first shaft 36 passes through a center of a first pulley 42, which is secured to the first shaft 36 to rotate with the first shaft 36 about the first axis. The first pulley 42 is secured to the first end 22 of the cable 12. A driving gear 44 is secured to a lower end of the first shaft 36 for rotation therewith.

The second shaft 38 extends parallel to the first shaft 36 and the second shaft 38 is configured to rotate about a second vertical axis along a longitudinal length of the second shaft 38. A driven gear 46 is secured to a lower end of the second shaft 38 and is configured to rotate about the second axis with the second shaft 38. The driven gear 46 is enmeshed with the driving gear 44, which drives the driven gear 46 and rotates the second shaft 38 when the first shaft 36 rotates. However, the direction of rotation of the first and second shafts 36 and 38 is opposite (i.e., clockwise and counterclockwise or vice versa depending on the direction of movement of the motor). The second shaft 38 extends through a center of a second pulley 48, which is secured to the second shaft 38 for rotation with the second shaft 38 about the second axis. The second end 24 of the cable 12 is secured to the second pulley 48. An upper end of the second shaft 38 is preferably supported by a housing of the motor 30. As a result of the gearing of the transmission system 34, when the motor 30 operates so as to rotate the driving bevel gear 33 in a clockwise direction, the first shaft 36 and first pulley 42 are rotated clockwise, and the second shaft 38 and the second pulley 48 are rotated counter-clockwise so that a certain length of the cable 12 from its respective ends 22 and 24 will be taken up by the respective pulleys, which will draw the pads 14 radially inward relative to opening 1c to cause compression of the breast 4. When the motor 30 reverses direction, the cable 12 slackens (relaxes) allowing the compressed breast 4 to relax and decompress. As the breast 4 decompresses, the tissue of the breast 4 pushes the pads 14 radially outwardly, while at least some of the length of the cable 12 taken up during compression is withdrawn from the pulleys 42 and 48.

Each tensioning and relaxation of the cable 12 which results in compression and permits decompression of the breast may be considered a cycle, which is preferably repeated to effect a breast tissue manipulation, which may cause breast milk expression. Parameters of the cycle(s) can be controlled by the controller 2. For example, the controller 2 may be configured to control the duration of compression and the duration of decompression, which may be the same or different. Also, the controller 2 may be configured to control the tension of the cable 12 during compression (which can control the pressure applied to the breast). The controller 2 has switches and buttons 2a and 2b, which may control the operating parameters as well as to turn the expression apparatuses on and off.

The controller 2 may be configured to operate based on set operating parameters or a real-time operating state of a breast pump apparatus that may be used simultaneously with the system 100 by the user, as discussed above. For example, the user of the system 100 may use the controller 2 to a select a manipulation speed or pressure, such as with the buttons 2a, 2b, based on the operating state of the breast pump to achieve a desired breast pumping result. Specifically, the user may select a certain compression and decompression duration and/or compression pressure based on a breast pumping speed and/or breast pumping pressure setting of the breast pump apparatus to achieve, for example, optimal milk flow rate or a desired level of comfort.

Alternatively or additionally, the controller 2 may be communicatively coupled (via wired or wireless connection) to a computing device 13 (FIG. 1), such as personal computer, smart phone, smart watch, or tablet computer, which can set and control the operation of the expression apparatus(s) 1. The computing device 13 may be coupled to a graphical display device (e.g., a screen). The computing device 13 may execute software (e.g. an application, a.k.a., an "app") that causes the display device to graphically display an operational interface to a user. The operational interface may be used to configure and/or control the expression apparatuses 1. For example, the operational interface may include virtual controls (e.g., on-screen buttons) that may replicate the physical buttons 2a, 2b of controller 2, and may provide information to the user about an operating status of the system 100. By way of example, and not limitation, such information may include current operating setting(s), elapsed time of use, heater temperature level, and breast skin temperature. The provided information may be saved locally or remotely for retrieval and/or analysis.

In one embodiment, the controller 2 may be communicatively coupled (via a wired or wireless connection interface) to a breast pump apparatus to automatically control the operation of the system 100 based upon the operation of the breast pump apparatus. For example, the controller 2 may automatically synchronize the operation of one or both expression apparatuses 1 of the system 100 with the breast pump apparatus based on feedback received directly from the breast pump apparatus or from a user of the breast pump apparatus. In one embodiment, a closed-loop feedback system may include a sensor that monitors a rate of milk production of the breastfeeding apparatus. The rate of milk production can be used as an input to the controller 2 as a basis to adjust operating parameters and settings of the system 100 so as to regulate the rate of milk production.

Figure 7:
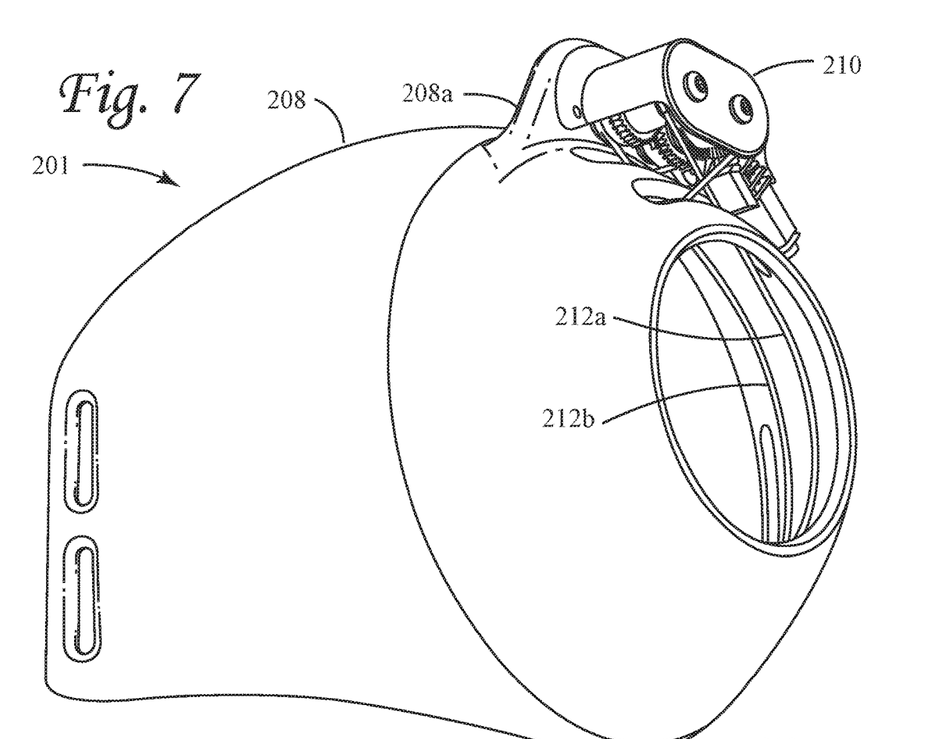
FIG. 7 shows a perspective view of another embodiment of a breast milk expression apparatus.
Figure 8:
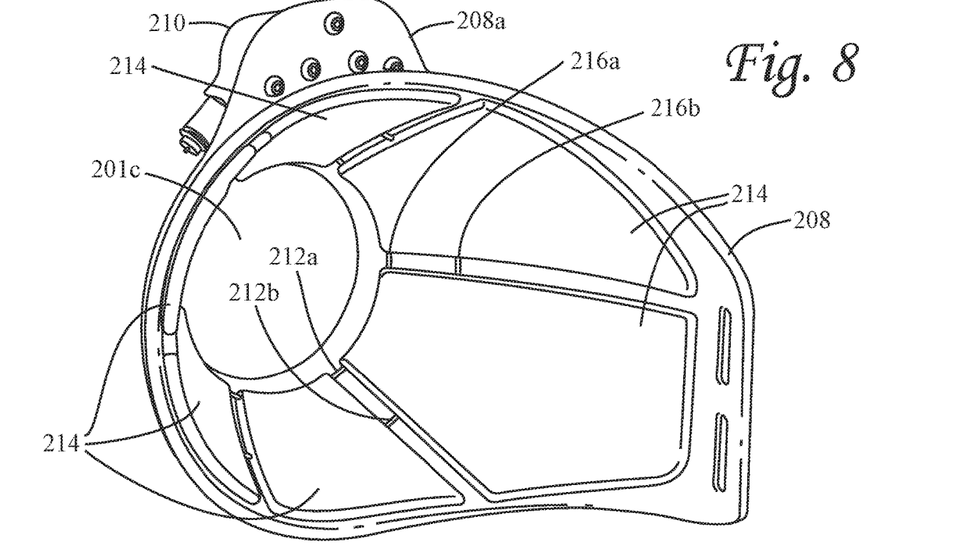
FIG. 8 shows a view of the breast milk expression apparatus of FIG. 7 from an inner side thereof.
Figure 9:
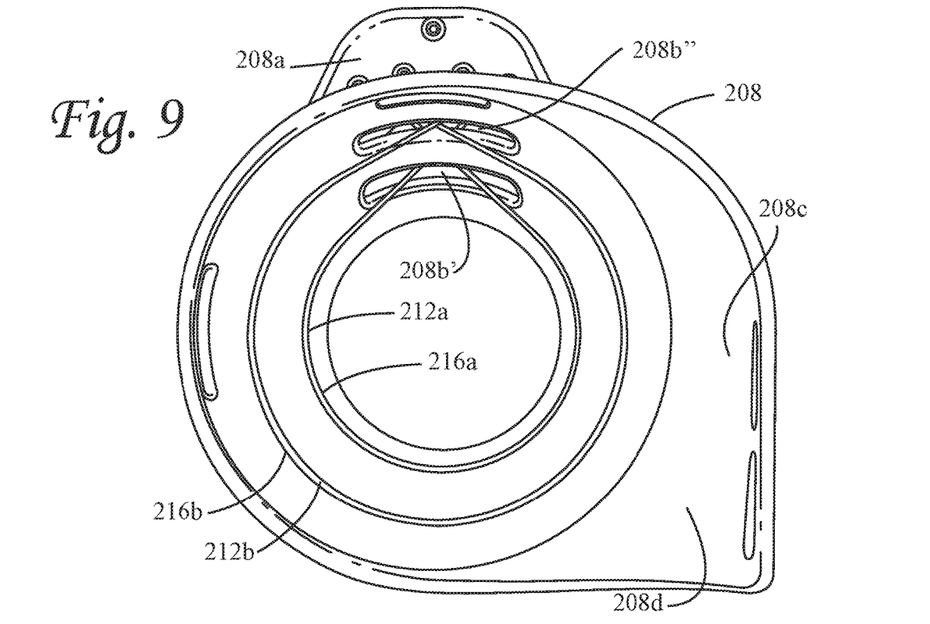
FIG. 9 shows the breast milk expression apparatus of FIG. 8 with pads removed therefrom to show details of an outer shell of the breast milk expression apparatus.
Figure 10:
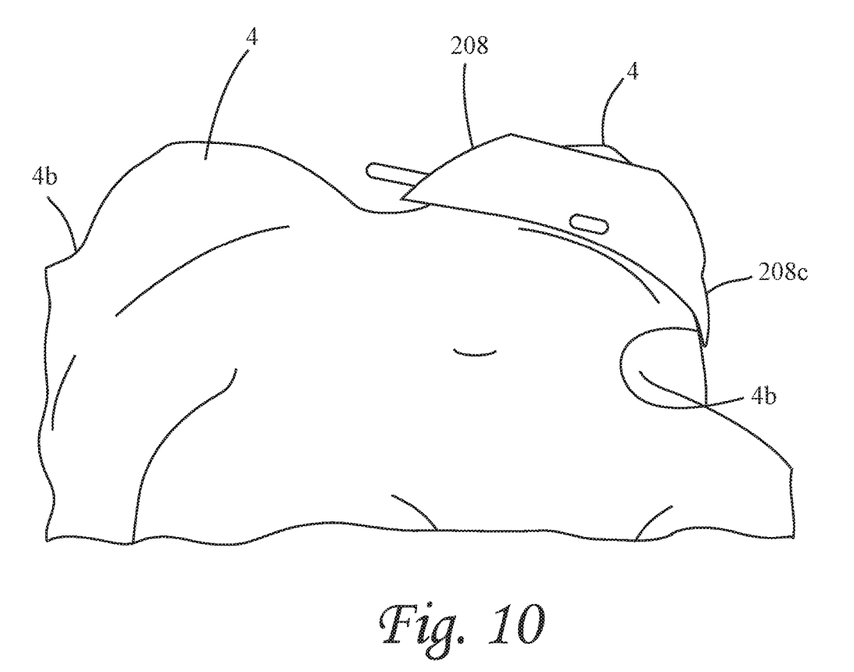
FIG. 10 shows the breast milk expression apparatus of FIG. 7 positioned on a breast.

An example of an embodiment of an expression apparatus 201 having multiple cable channels, grooves, and cables is shown in FIGS. 7 to 9. The expression apparatus 201 has the same function as the expression apparatus 1, but differs in structure in that the expression apparatus 201 includes a plurality of cable channels, grooves, and cables, further details of which are provided below. In the embodiment of the expression apparatus 201, elements corresponding to expression apparatus 1 are incremented by "200". Thus, as shown in FIG. 7, the expression apparatus 201 has an outer shell 208 with a deck 208a that supports a drive unit 210.

As shown in FIG. 8, the expression apparatus 201 has a plurality of pads 214 on an inner side of the outer shell 208. The pads 214 have a plurality of channels 216a and 216b through which corresponding cables 212a and 212b extend. For each pad 214, channel 216a is spaced from channel 216b, and channel 216a is located closer to opening 201c in the expression apparatus 201 than channel 216b.

Figure 7A:
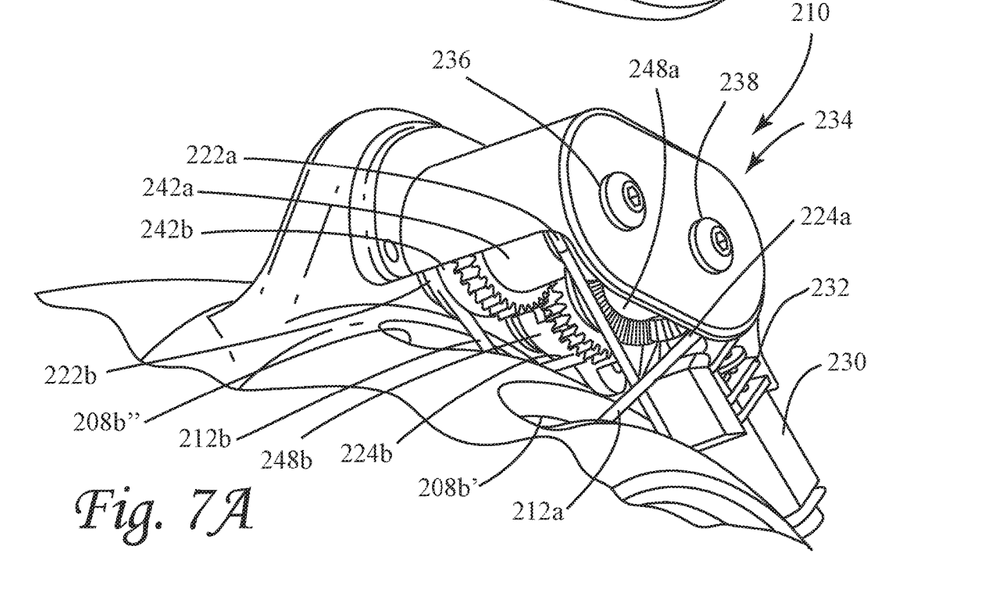
FIG. 7A shows an exploded view of a portion of the breast milk expression apparatus of FIG. 7.

The outer shell 208a defines openings 208b' and 208b" through which corresponding cables 212a and 212b extend, as shown in FIGS. 7, 7A, and 9. As shown in greatest detail in FIG. 7A, cable 212a has ends 222a and 224a that are routed to a transmission system 234 of the drive unit 210. The drive unit 210 includes an electric motor 230, a gearbox 232 driven by the motor 230, and the transmission system 234 driven by the motor 230. End 222a is routed to a pulley 242a on shaft 236 of the transmission system 234 and end 224a is routed to a pulley 248a on shaft 238 of the transmission system 234. The other cable 212b has ends 222b and 224b that are routed to the transmission system 234 of the drive unit 210. Specifically, end 222b is routed to a pulley 242b on shaft 236 and end 224b is routed to a pulley 248b on shaft 238. The shafts 236 and 238 correspond to shafts 36 and 38 of drive unit 10 and shafts 236 and 238 are coupled together and driven by a geared arrangement in the same manner as shafts 36 and 38. Thus, a detailed description of the drive unit 210 and its operation in driving shafts 236 and 238 with the motor 230 and gearbox 232 is omitted for brevity. As noted above, the operation of the expression apparatus 201 is the same as for expression apparatus 1. When the drive unit 210 is operating in one direction, it tensions both of the cables 212a and 212b around the pads 214 to compress the breast. When the drive unit 210 reverses direction, cables 212a and 212b loosen (relax) and permit the breast to decompress.

There have been described and illustrated herein several embodiments of a breast milk expression system and apparatus. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other suitable materials may be used as well. In addition, while particular types of driving units have been disclosed, it will be understood that other arrangements of driving units can be used, such as, by way of example, and not by way of limitation, a motorized worm drive, and an electro-magnetic solenoid. Also, while a system having two expression apparatuses is preferred, it will be recognized that a single expression apparatus system may also be used. Moreover, while particular configurations have been disclosed in reference to the straps used to position the expression apparatuses, it will be appreciated that other configurations could be used as well. It will therefore be appreciated by those skilled in the art that yet other modifications could be made to the provided invention without deviating from its spirit and scope as claimed.

What is claimed is:
1. A breast milk expression apparatus comprising:
an outer shell;
a plurality of circumferentially spaced inner pads coupled to the outer shell, the plurality of pads disposed under the outer shell, each pad having a radially inner concave surface configured to engage a breast of a user, and the pads configured for radial displacement, wherein each pad defines a circumferential channel extending longitudinally along a respective axis, and wherein in a configuration where the pads engage the breast of the user, the pads are disposed between the outer shell and the breast;
a compression unit coupled to the plurality of pads, configured to cyclically displace the pads radially inwardly against the breast to cause compression of the breast and, following compression of the breast, permitting the breast to expand and decompress, wherein the compression unit includes:
a cable banded about and extending longitudinally and coaxially through each circumferential channel of the plurality of pads, wherein the circumferential channels permit relative longitudinal movement of the cable relative to the pads, and
a drive unit coupled to the cable and the outer shell, the drive unit configured to tighten the cable about the pads to cause the pads to compress the breast and configured to loosen the cable about the pads, permitting the breast to expand and decompress.
2. The apparatus according to claim 1, wherein:
the outer shell defines a central opening about which the plurality of inner pads are circumferentially spaced, wherein the central opening is dimensioned to receive a breast pump breastshield therethrough for engagement with the user's breast.
3. The apparatus according to claim 1, further comprising:
a cover configured to at least partially cover the outer shell, the plurality of pads, and the compression unit.
4. The apparatus according to claim 1, wherein:
the outer shell has an inner generally concave surface facing outer surfaces of the plurality of pads.
5. The apparatus according to claim 4, wherein:
the inner surface of the outer shell has a portion that is convex near an axillary part of the breast.
6. The apparatus according to claim 1, wherein:
the outer shell has an outer surface and a deck extending from the outer surface, wherein the deck supports and is connected to the drive unit.
7. The apparatus according to claim 1, wherein:
the drive unit includes an electric motor configured to drive a transmission system to cyclically tension and relax the cable.

8. The apparatus according to claim 1, wherein:
the drive unit is configured to receive at least one of power and control setting signals from a controller.

9. The apparatus according to claim 1, wherein:
the drive unit is configured to vary at least one of a pressure applied by the pads to the breast, a duration of compression and decompression, and a heating level of the pads.

10. The apparatus according to claim 1, wherein:
at least one of the plurality of pads is heated.

11. The apparatus according to claim 1, wherein:
at least one of the pads and the outer shell are made of a polymeric material from the group consisting of ABS, nylon, polyurethane, and silicone.

12. The apparatus according to claim 11, wherein:
at least one of the pads and the outer shell have a Shore hardness of 10 A to 90 D.

13. A breast milk expression system comprising:
at least one breast milk expression apparatus according to claim 1;
at least one strap coupled to the breast milk expression apparatus and configured to position the breast milk expression apparatus on a user's breast; and
a controller configured to control the operation of the breast milk expression apparatus.

14. The system according to claim 13, wherein:
the controller is configured to control at least one of a pressure applied by the pads to the breast, a duration of compression and decompression, and a heating level of the pads.

15. The system according to claim 13, wherein:
the controller is a wired or wireless controller.

16. The system according to claim 13, wherein:
the breast milk expression apparatus includes a power supply to power at least one of the milk expression apparatus and the controller.

17. The system according to claim 13, wherein:
the controller includes a power supply to power at least one of the controller and the breast milk expression apparatus.

18. A breast milk expression system comprising:
two breast milk expression apparatuses according to claim 1;
a plurality of straps coupled to the breast milk expression apparatuses and configured to position the breast milk expression apparatus on corresponding breasts of the user, the plurality of straps being adjustable for fitting to a body of the user; and
a controller configured to control the operation of at least one of the two breast milk expression apparatuses.

19. A breast milk expression apparatus comprising:
an outer shell;
a plurality of circumferentially spaced inner pads coupled to the outer shell, the plurality of pads disposed under the outer shell, each pad having an inner concave surface configured to engage the breast of the user, and the pads configured for radial displacement, and wherein in a configuration where the pads engage the breast of the user, the pads are disposed between the outer shell and the breast;
a compression unit comprising a cable banded about coupled to the plurality of pads, the compression unit configured to cyclically displace the pads radially inwardly against the breast to cause compression of the breast and, following compression of the breast, permitting the breast to expand and decompress.

\* \* \* \* \*